United States Patent [19]

Warning et al.

[11] 4,123,434
[45] Oct. 31, 1978

[54] PROCESS FOR PREPARING TRIMERIC Δ¹-PIPERIDEINS AND TRIMERIC 1-PYRROLINE

[75] Inventors: Klaus Warning, Liederbach; Michael Mitzlaff, Bad Homburg, both of Fed. Rep. of Germany

[73] Assignee: Hoechst Aktiengesellschaft, Frankfurt am Main, Fed. Rep. of Germany

[21] Appl. No.: 823,155

[22] Filed: Aug. 9, 1977

[30] Foreign Application Priority Data

Aug. 11, 1976 [DE] Fed. Rep. of Germany ....... 2636098

[51] Int. Cl.² .................... C07D 213/22; C07D 207/20
[52] U.S. Cl. ............................ 260/296 D; 260/290 P; 260/290 H; 260/313.1
[58] Field of Search ............. 260/296 D, 290 P, 313.1

[56] References Cited
PUBLICATIONS van Noordwijk et al., Recueil, vol. 82, pp. 763-772 (1963).
Grisar et al., Journal of Med. Chem., vol. 19, No. 10, pp. 1195-1201 (1976).

Primary Examiner—Alan L. Rotman
Attorney, Agent, or Firm—Curtis, Morris & Safford

[57] ABSTRACT

Trimeric piperideins and trimeric pyrrolidine are prepared by saponification of 1-acyl-2-alkoxypiperidines or pyrrolidines of the general formula

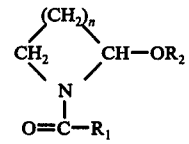

in which $n$ means 2 or 3
$R_1$ represents hydrogen or a linear or branched $C_1$–$C_4$ alkyl radical and
$R_2$ represents a linear or branched $C_1$–$C_4$ alkyl radical in aqueous and/or alcoholic solution in known manner in the presence of a strong acid or base and trimerizing the reaction product at a pH equal to or greater than 8. The compounds are valuable intermediates for the manufacture of alkaloids and other pharmaceutically effective substances and N-heterocycles.

6 Claims, No Drawings

PROCESS FOR PREPARING TRIMERIC Δ¹-PIPERIDEINS AND TRIMERIC 1-PYRROLINE

This invention relates to the preparation of trimeric, aliphatic nitrogen bases

Δ¹-piperidein (2,3,4,5-tetrahydropyridine) 

is unstable at room temperature in its free form and trimerizes spontaneously to form a triazine derivative, i.e. α-tripiperidein (cf. C.Schöpf et al. Liebigs Ann.-Chem. 559, 1, (1948) of the formula

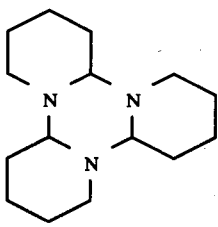

In aqueous solution of pH 9 to 10 α-tripiperidein is transformed at 25° C. in a reaction of first order in a yield of 90% into isotripiperidein, i.e. a hexahydropyrimidine derivative (cf. C.Schöpf et al., Chem. Ber. 85, 937 (1952) and 89, 335 (1955)) of the formula

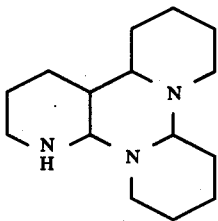

These two trimers of Δ¹-piperidein are very important as intermediates. They are used, for example, in the synthesis of numerous alkaloids such as orensine, isopelletierine, lupinine, anaferine, anahygrine, and alkaloids of lythraceae, and to prepare derivatives of these natural substances, which have in part pharmacologically interesting properties (lupinine derivatives and isopelletierine derivatives, for example, having an anthelmintic effect). Nitrogen-containing bicyclic systems, natural polyene carboxylic acid amides, homotryptamines, 2-piperidyl-methyl ketones, 2-azacycloalkylmethyl-substituted phenyl carbinols and ketones with anticoagulative effect, as well as 2-cyanopiperidine and 1-acetyl-1,2,3,4-tetrahydropyridine have also become readily accessible by syntheses using the trimers of Δ¹-piperidein.

1-Pyrroline is likewise an important component of syntheses, which is used, for example, for the preparation of prodigiosin, of pyrrolizidines and 2-azacycloalkylmethyl-substituted phenyl carbinols and ketones having an anticoagulative effect. 1-Pyrroline, too, trimerizes to give a product the constitution of which has not yet been clarified completely.

Owing to their key position in the preparative chemistry of nitrogen-containing heterocyclic compounds processes for the manufacture of trimeric Δ¹-piperideins and of trimeric 1-pyrroline are of considerable industrial importance.

The known methods for preparing α-tripiperidein and 1-pyrroline, however, yield these compounds in a moderate yield only and, due to the use of partly dangerous chemical substances, the handling of which is rather unpleasant, for example perchloryl fluoride (D. M. Gardner, R. Helitzer and D. H. Rosenblatt, J.Org. Chem. 32, 1115 (1967)), N-chloropiperidine (C. Schöpf et al., Liebigs Ann.Chem. 559, 1 (1948)), and N-chloropyrrolidine (D. W. Fuhlhage and C. A. VanderWerf, J.Am. Chem. Soc. 80, 6249 (1958)), they can be used on a laboratory scale only. In the process for the manufacture of α-tripiperidein and 1-pyrroline on an industrial scale, as described in German Pat. No. 1,054,088, N-chloropiperidine and N-chloropyrrolidine are obtained in benzenic solution which must be kept at a temperature below 0° C. in order to suppress spontaneous decomposition of the said compounds, occasionally taking place with deflagration. The danger arising from the use of N-chloro compounds is reported, for example, in HoubenWeyl, Methoden der organischen Chemie, volume V/3, page 796.

Isotripiperidein which is equally important as intermediate has been produced up to now either by transformation of α-tripiperidein at pH 9 to 10 in aqueous solution (loc. cit) or by dehydrogenation of piperidine in the presence of a catalyst (cf. DT-PS No. 911,263). In the latter process high reaction temperatures of from 300° to 700° C., preferably 530° C., are required and the catalyst gradually loses its activity.

A further drawback of the aforesaid process is the low conversion of the piperidine (37%) and the formation of pyridine as by-product, which necessitate a complicate and expensive distillation.

It is, therefore, desirable to provide a more simple and more economic process for the manufacture of trimeric Δ¹-piperideins and of trimeric 1-pyrroline, wherein no dangerous and unpleasant starting materials are used. This problem is solved by the invention.

It is the object of the present invention to provide a process for the manufacture of trimers of aliphatic and cyclic nitrogen bases of the general formula

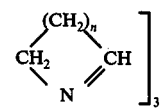 I in which $n$ means 2 or 3, which comprises saponifying 1-acyl-2-alkoxypiperidines or pyrrolidines of the general formula

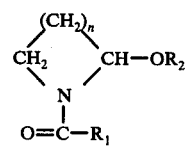 II in which $n$ means 2 or 3
$R_1$ represents hydrogen or a linear or branched $C_1$–$C_4$ alkyl radical and
$R_2$ represents a linear or branched $C_1$–$C_4$ alkyl radical in aqueous and/or alcoholic solution in known manner in the presence of a strong acid or base and trimerizing the reaction product at a pH equal to or greater than 8.

When trimeric Δ¹-piperideins (n being 3 in formula I) are to be produced, an alcohol of the formula R₂OH can first be split off, prior to saponification and trimerization, either thermally or catalytically under the conditions described in GB-PS No. 1,125,324 from the 1-acyl-2-alkoxy-piperidines used as starting compounds. In this reaction 1-acyl-Δ²-piperideins of the formula

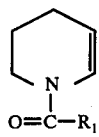

(III)

are formed which are then subjected to saponification and trimerization under the same conditions as compounds II. In this reaction the double bond moves from the Δ²-position to the Δ¹-position.

The radicals R₁ and R₂, which are eliminated during the course of the reaction, are not critical and may also contain more than 4, for example up to 10 carbon atoms, and possibly also reaction inert atoms or groups, for example F or NO₂. Preference is given, however, to unsubstituted alkyl radicals having from 1 to 4 carbon atoms. Because of their easier production compounds in which R₂ has 1 to 2 carbon atoms are preferred and also those in which R₁ stands for hydrogen.

As starting compound in the process of the invention there is used as 1-acyl-2-alkoxypiperidine or pyrrolidine of the formula II, which is preferably obtained by electrochemical alkoxylation of 1-acyl-piperidine or pyrrolidine. The latter compounds can be obtained, for example, by reacting piperidine or pyrrolidine with an acylating agent, for example an acid chloride, an acid anhydride or an ester; there are mentioned, for example, the reactions of piperidine with a formic acid methyl ester (K. Auwers, Z.f. physik. Chemie, 15, 45 (1894) or acetic anhydride (A. W. Hofmann, Ber.Deut.Chem.Ges., 16, 588 (1883), in which 1-formylpiperidine or 1-acetyl-piperidine is obtained in a yield of about 96%.

The use of C₁-C₄ carboxylic acid esters with C₁-C₄ alcohols as acylating agents offers the special advantage that, in addition to the desired 1-acylpiperidine or pyrrolidine, only alcohol is formed as by-product, which need not be separated from the 1-acylpiperidine or pyrrolidine by distillation and can serve as reactant or solvent in the subsequent electrochemical alkoxylation.

The electrochemical alkoxylation is preferably carried out, for example, by the process of DT-OS No. 2,539,777, wherein N-acyl-piperidines or pyrrolidines of the general formula

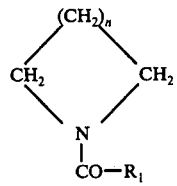

IV are anodically alkoxylated in a C₁-C₄ alcohol, preferably methanol, in the presence of at least one tetraalkyl ammonium tetrafluoroborate, hexafluorophosphate or nitrate as conducting salt in an electrolytic cell with stationary or flowing electrolyte, at a temperature of from about −10° to +100° C., preferably about 0° to +60° C. The amount of current used should be in the range of from about 2 to 2.5 faradays for each mol of starting compound IV and the concentration of conducting salt in the electrolysis solution amounts to about 0.01 to 2.0, preferably 0.02 to 1.0, mol/l. The molar proportion of starting compound IV to alcohol in the electrolysis solution is in the range of from about 1:1 to about 1:100, preferably about 1:2 to about 1:60 and more preferably about 1:5 to about 1:50. After having passed through the desired amount of current, the electrolysis current is switched off, the reaction mixture removed from the electrolytic cell is freed from the conducting salt and worked up in known manner, preferably by distillation.

The compounds of formulae II and III are saponified in known manner in aqueous and/or alcoholic solution in the presence of a strong acid or base. When the saponification is carried out in aqueous alcoholic or purely alcoholic solution, C₁-C₄ alcohols are preferred, especially methanol and possibly also ethanol.

Suitable acids are strong mineral acids, in alcoholic solution preferably hydrogen halides such as hydrogen bromide and preferably hydrogen chloride. When the reaction is carried out in aqueous solution, other strong acids may also be used, especially mineral acids such as sulfuric acid.

Preferred bases are hydroxides and/or alcoholates of alkali metals, especially of potassium or sodium, i.e. preferably sodium hydroxide, potassium hydroxide and, when working in alcoholic solution, the corresponding alcoholates.

The saponification can be carried out in two ways, depending on the chosen saponification medium.

According to process A the saponification is carried out in the aqueous and/or alcoholic solution of a strong acid. When operating in an aqueous medium the acyl radical at the nitrogen atom is split off in the form of the corresponding carboxylic acid R₁COOH and, when operating in an alcoholic medium, it is split off in the form of the ester of said carboxylic acid with the alcohol used as solvent. The de-acylated nitrogen heterocycle thus forms a salt with the acid used, from which salt cyclic nitrogen bases having a C=N double bond are set free with alkalies, with splitting off of R₂OH, provided that the R₂OH has not yet been split off thermally or catalytically by the process disclosed in GB-PS No. 1,125,324. The nitrogen bases thus obtained unite in known manner to give the trimers of Δ¹-piperidein or 1-pyrroline.

According to process B saponification is carried out in the aqueous or alcoholic solution of a strong base, wherein the acyl radical at the nitrogen atom is split off in the form of the salt of the carboxylic acid R₁COOH with the base used, and, as described for process A, cyclic nitrogen bases with a C=N double bond are set free, which unite in known manner to give the trimers of Δ¹-piperidein or 1-pyrroline.

When process A is carried out in an alcoholic medium, it could be represented by way of example by the following reaction equation, in which a possible splitting off of R₂OH according to the aforesaid GB-PS No. 1,125,324 is not taken into consideration.

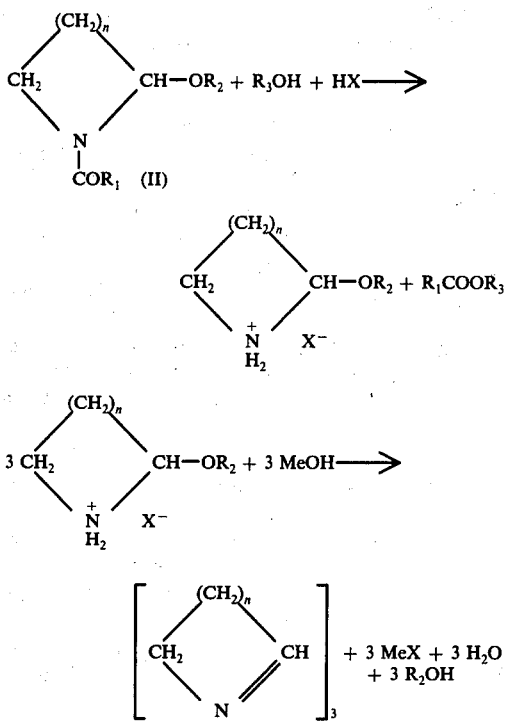

Process B in an aqueous medium is illustrated by the following equation 3; in this case, too, a possible splitting off of $R_2OH$ according to GB-PS No. 1,125,324 not being taken into consideration.

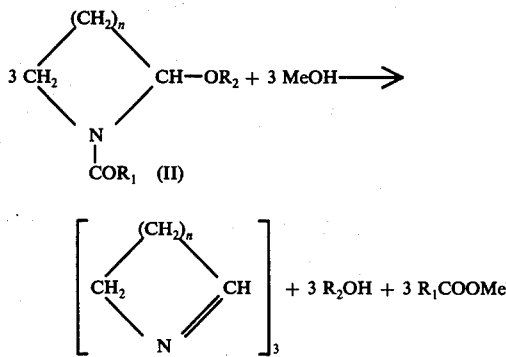

In the aforesaid formulae $R_1$, $R_2$ and $n$ have the same meanings as in formulae I to III, X represents an inorganic or organic acid radical, Me represents an alkali metal or alkaline earth metal equivalent and $R_3$ in equation (1) is a linear or branched $C_1$–$C_4$ alkyl radical.

In all cases, the reaction temperature is in the range of from about 40° to 100° C., preferably 60° to 80° C., the reaction period being in the range of from about 4 to 8 hours, depending on the reaction temperature. The volume of the saponification medium is not critical. It is chosen in usual manner, for example about 2 to 10, especially about 3 to 5 parts by volume for 1 part by weight of the compound of formula II.

When working according to process A about 1 to 10, preferably about 1 to 2 and more preferably about 1.3 to 1.7 mols of acid are used for each mol of 1-acyl-2-alkoxypiperidine, pyrrolidine or 1-acyl-$\Delta^2$-piperidein. The amount of acid is chosen, inter alia, under the consideration that a large excess thereof would require a correspondingly larger amount of base in the following process step.

By adding ether to the alcoholic solution of the salts formed in the process of the invention the 2-alkoxy-piperidinium salts according to equation (1) can be isolated in crystallized form and from the isolated salt trimeric $\Delta^1$-piperidein can then be obtained in alcaline solution in the following stage according to equation (2).

According to a preferred embodiment of process A, the solution of the piperidinium or pyrrolidinium salts, as obtained after saponification with acid of the 1-acyl-2-alkoxy-piperidines or pyrrolidines or — if $R_2OH$ is split off by the process of GB-PS No. 1,125,324 — of the 1-acyl-$\Delta^2$-piperideins, is directly used for the alkalization in the subsequent stage.

The alkalization can be carried out in simple manner by adding dropwise the acid solution of the salts obtained in the preceding stage to an aqueous or alcoholic solution of an alkali and optionally refluxing the mixture for about 2 to 4 hours to complete the reaction. In this reaction about 1.1 to 10, preferably 1.3 to 2 mols of alkali are used for 1 mol of acid used. Preferred alkalis are alkali metal or alkaline earth metal hydroxides, especially sodium or potassium hydroxide. As alcohols $C_1$–$C_4$ alcohols are preferred, in particular methanol and possibly also ethanol.

For working up, the alcohol is distilled off, the residue taken up in aqueous alkali, the aqueous solution is extracted with a solvent immiscible with water such as an ether or a chlorinated hydrocarbon, especially dichloromethane, and the solvent is distilled off, if necessary under reduced pressure.

After said treatment, a residue of trimers of formula I remains behind. This crude product has a sufficient purity for many applications, but it may be further purified by distillation or recrystallization, for example from acetone.

In process B, alkali metal and alkaline earth metal hydroxides or alcoholates are also used preferably as alkalis, for example sodium hydroxide, potassium hydroxide or sodium methylate. About 1.1 to 10 mols, preferably about 1.3 to 1.8 mols of alkali are used for each mol of 1-acyl-2-alkoxy-piperidine, pyrrolidine or 1-acyl-$\Delta^2$-piperidein. The reaction is carried out at a temperature of from about 40° to 100° C., preferably at the boiling point of the solvent. When the alkaline saponification is terminated, the trimeric $\Delta^1$-piperidein or 1-pyrroline can be obtained by extracting the aqueous phase with ether or a chlorinated hydrocarbon, for example dichloromethane, in the same manner as described above for the working up of the product obtained according to process A.

Whereas in the preparation of trimeric pyrroline each variant of the process of the invention yields the same final product, it should be taken into consideration in the preparation of trimeric piperidein from compound II or III that α-tripiperidein is unstable at pH 8 to 11, more particularly 9 to 10, and irreversibly forms isotripiperidein. Hence, if pure α-tripiperidein is desired, this pH range should be avoided as far as possible. This means that the acid alcoholic saponification mixture must be alkalized with a sufficient amount of alkali, preferably about 1.5 to 2 mols of alkali for one equivalent of acid and, moreover, as a preferred feature, the acid alcoholic solution should be added slowly while thoroughly stirring, to avoid local overconcentrations, preferably at the reaction temperature, to the alcoholic alkali in order that the critical pH range is passed as rapidly as possible. Surprisingly, when acid aqueous saponification mixtures are treated in the same manner, i.e. pouring into aqueous alkali at reaction temperature, isotripiperidein is preponderantly obtained. Accordingly, if alcohol-water mixtures are used, which are not preferred with regard to the working up, mixtures of α- and isotripiperidein are obtained. As compared therewith, the alkaline saponification at a sufficiently high pH (above 11) yields exclusively α-tripiperidein, irrespective of whether the reaction is carried out in an alcoholic or aqueous medium, the latter being preferred on account of the good yields and the easy working up.

The following examples illustrate the invention. Examples (a), (b) and (c) at the beginning describe by way of example the preparation of the starting compounds II.

(a) Preparation of 1-formyl-2-methoxy-piperidine

A mixture of
169.8 g of N-formyl-piperidine and
495.3 g of methanol
in which 2.41 g of tetramethylammonium tetrafluoroborate are dissolved as conducting salt is introduced into an electrolytic cell as shown in the drawing of DT-OS No. 2,113,338 provided with cover and reflux condenser and having a capacity of about 1000 ml. Two concentrically arranged platinum net cylinders having 225 meshes per square centimeter and a diameter of 24 and 36 mm, respectively, at a height of 95 cm are immersed as electrodes in the solution, the outer electrode being connected as anode. During electrolysis, the temperature is maintained at about 20° C. After having switched on the electrolysis current, the current density at the anode is 3 A/dm². After having passed 2.0 faradays per mol of N-formylpiperidine, the current is switched off. The calculated average cell voltage is 21.7 volts.

After working up of the elctrolysis solution in known manner, 199.6 g of 1-formyl-2-methoxypiperidine (boiling point 50° C. under 0.13 mbar; $n_D^{25}$ = 1.4718) are obtained, corresponding to a material yield of 92.9% and a current efficiency of 92.9%.

(b) Preparation of N-formyl-2-methoxy-pyrrolidine

Under the conditions specified sub (a)
17.7 g of N-formyl-pyrrolidine and
57.2 g of methanol
are electrolyzed in the presence of 0.29 g of tetramethylammonium tetrafluoroborate as conducting salt. After having passed 2.0 faradays for each mol of N-formyl-pyrrolidine, the current is switched off. The calculated average cell voltage is 28.8 volts. Working up of the electrolysis solution yields 20.0 g of 1-formyl-2-methoxypyrrolidine (boiling point 39°–40° C./0.1 mbar; $n_D^{25}$ = 1.4700, corresponding to a material yield of 86.6% and a current efficiency of 86.6%.

(c) Preparation of N-acetyl-2-methoxypyrrolidine

Under the conditions specified sub (a) and (b)
19.6 g of N-acetylpyrrolidine and
55.6 g of methanol
are electrolyzed in the presence of 0.28 g of tetramethylammonium tetrafluoroborate as conducting salt. After having passed 2.0 faradays per mol of N-acetyl-pyrrolidine, the current is switched off. The calculated average cell voltage is 32.7 volts. Working up of the electrolysis solution yields 19.9 g of 1-acetyl-2-methoxy-pyrrolidine (boiling point 53° C./0.1 mbar; $n_D^{25}$ = 1.4674), corresponding to a material yield of 80.0% and a current efficiency of 80.0%.

EXAMPLE 1

28.6 g (0.2 mol) of 1-formyl-2-methoxy-piperidine were refluxed for 4 hours together with 0.3 mol of methanolic HCl. 28 g (92.4% of the theory) of 2-methoxy-piperidinium chloride melting at 93°–95° C. were precipitated in crystalline form by the addition of absolute diethyl ether. According to literature the melting point is 94°–96° C. (cf. C. Schopf et al., Chem.Ber. 93, 2457 (1960)).

15.15 g (0.1 mol) of 2-methoxy-piperidinium chloride were dissolved in 20 ml of about 0.1N methanolic HCl and the solution was added dropwise to a solution of 9.9 g KOH (85% strength, 0.15 mol) in methanol. The mixture was refluxed for 4 hours and the precipitated KCl removed by suction filtration. The alcohol was then removed under reduced pressure, the residue taken up in about 2% aqueous potassium hydroxide solution, the aqueous phase extracted with ether, and the ether phase dried over sodium sulfate. After removal of the solvent, 7 g (84.3% of the theory) of α-tripiperidein melting at 51° to 54° C. were obtained. By recrystallization from acetone the pure compound was obtained melting at 57° to 60° C.

EXAMPLE 2

28.6 of (0.2 mol) of 1-formyl-2-methoxy-piperidine were stirred for 8 hours at 60° C. together with 150 ml of 2N hydrochloric acid. Next, the reaction mixture was added dropwise to a solution of 33 g of KOH (85% strength, 0.5 mol) in 50 ml of water and the whole was refluxed for 4 hours. After extraction of the aqueous phase with dichloromethane 16.3 g (98.2% of the theory) of isotripiperidein melting at 87°–91° C. were obtained. When recrystallized from acetone the product had a melting point of 91°–93° C.

EXAMPLE 3

31.4 g (0.2 mol) of 1-acetyl-2-methoxy-piperidine were refluxed for 4 hours together with 0.3 mol of methanolic HCl. Next, the reaction mixture was dropped into a solution of 22 g KOH (85% strength, 0.33 mol) in methanol and the mixture was again refluxed for 4 hours. The precipitated KCl was removed by suction filtration, the alcohol eliminated under reduced pressure, the oily residue taken up in about 2% sodium hydroxide solution and exhaustively extracted with dichloromethane. The extract (12.6 g of an oil) was distilled under reduced pressure (boiling point 120° C. to 170° C./0.3 mbar). 7.8 g (47% of the theory) of iso-tripiperidein were obtained which solidified on prolonged standing and melted at 95° C.

EXAMPLE 4

28.6 g (0.2 mol) of 1-formyl-2-methoxypiperidine and 0.3 mol of methanolic HCl were refluxed for 6 hours and the reaction mixture was then added dropwise to a solution of 33 g of KOH (85% strength, 0.5 mol) in methanol and the whole was refluxed again for 4 hours. After distilling off of the solvent, taking up of the residue in about 2% KOH and extracting with dichloromethane, 13.0 g (78.3% of the theory) of α-tripiperidein melting at 55°–58° C. were obtained.

EXAMPLE 5

28.6 g (0.2 mol) of 1-formyl-2-methoxypiperidine and 0.3 mol of methanolic HCl were refluxed for 4 hours. At atmospheric pressure in a boiling range of from 30° to 50° C. a mixture of formic acid methyl ester and methanol, which could be re-used for the preparation of 1-formyl-piperidine, was distilled off. The distillation residue was added dropwise to a solution of 21.7 g of KOH (85% strength, 0.33 mol) in methanol and the whole was refluxed for 4 hours. Working up as described in Example 4 yielded 13.3 g (80.1% of the theory) of isotripiperidein melting at 87°–91° C.

EXAMPLE 6

28.6 g (0.2 mol) of 1-formyl-2-methyl-piperidine and 0.3 mol of methanolic HCl were refluxed for 4 hours and then the reaction mixture was added dropwise to a sodium methylate solution prepared from 11.5 g (0.5 mol) of sodium and 200 ml of absolute methanol. Working up under the conditions of Example 4 yielded 13.9 (83.7% of the theory) of α-tripiperidein melting at 58°–60° C.

EXAMPLE 7

28.6 g (0.2 mol) of 1-formyl-2-methoxy-piperidine and 0.2 mol of methanolic HCl were refluxed for 4 hours and then the reaction mixture was added dropwise to a solution of 33 g KOH (85% strength, 0.5 mol) in methanol. Working up under the conditions of Example 4 yielded 12.6 g (76% of the theory) of α-tripiperidein melting at 57°–59° C.

EXAMPLE 8

28.6 g (0.2 mol) of 1-formyl-2-methoxy-piperidine and 150 ml of 2N $H_2SO_4$ in water were stirred for 6 hours at 60° C. and then the reaction mixture was added dropwise to 33 g of KOH (85% strength, 0.5 mol) in 100 ml of water and the whole was refluxed for 1 hour. Extraction with dichloromethane yielded 15.5 g (93.4% of the theory) of isotripiperidein melting at 97°–99° C.

EXAMPLE 9

28.6 g (0.2 mol) of 1-formyl-2-methoxy-piperidine and 57 g (0.3 mol) of p-toluene-sulfonic acid monohydrate in 200 ml of absolute methanol were refluxed for 6 hours and then the reaction mixture was added dropwise to a solution of 21.7 g of KOH (85% strength, 0.33 mol) in methanol. After removal of the precipitated salt by suction filtration, removal of the solvent under reduced pressure, taking up of the residue in 2% potassium hydroxide solution and extracting with dichloromethane, 12.6 g (75.9% of the theory) of isotripiperidein melting at 94°–96° C. were obtained.

EXAMPLE 10

22.2 g (0.2 mol) of 1-formyl-$\Delta^2$-piperidein and 0.3 mol of methanolic HCl were refluxed for 4 hours and then the reaction mixture was added dropwise to a solution of 33 g of KOH (85% strength, 0.5 mol) in 100 ml of methanol. Working up under the conditions of Example 4 yielded 11.9 g (71.7% of the theory) of α-tripiperidein melting at 60° C.

The 22.2 g of 1-formyl-$\Delta^2$-piperidein used as starting compound in this example were prepared by the process of GB-PS No. 1,125,324 by stirring 35.3 g of 1-formyl-2-methoxy-piperidine and about 2.5 g of $Al_2O_3$ (acid) for 6 hours at 80° C. and distilling the reaction product under reduced pressure. The compound obtained had a melting point of 45° C./0.1 mbar Hg.

EXAMPLE 11

25 g (0.2 mol) of 1-acetyl-$\Delta^2$-piperidein and 0.3 mol of methanolic HCl were refluxed for 4 hours and then the reaction mixture was added dropwise to a solution of 33 g of KOH (85% strength, 0.5 mol) in 100 ml of methanol. Working up as described in Example 4 yielded 2 g (12% of the theory) of α-tripiperidein melting at 56° C.

The 1-acetyl-$\Delta^2$-piperidein used as starting compound in this example was prepared from 1-acetyl-2-methoxypiperidine in the same manner as the 1-formyl-$\Delta^2$-piperidein used in Example 10 from 1-formyl-2-methoxy-piperidine. 25 g of 1-acetyl-$\Delta^2$-piperidein melting at 59° C./0.2 mbar Hg were obtained from 32.7 g of 1-acetyl-2-methoxy-piperidine.

EXAMPLE 12

25.8 g (0.2 mol) of 1-formyl-2-methoxy-pyrrolidine were refluxed together with 0.3 mol of methanolic HCl and then the reaction mixture was added dropwise to a sodium methylate solution prepared from 11.5 g of sodium (0.5 mol) and 200 ml of absolute methanol. The methanol was distilled off, 25% sodium hydroxide solution added to the residue and the reaction product extracted with ether. After distillation of the ether, an oil (13.9 g) remained behind which was distilled under reduced pressure. The first runnings preponderantly consisted of 4-amino-butyraldehyde dimethyl acetal (4.2 g). The main fraction distilled over at 150°–160° C./15 mbar (6.1 g, 44% of the theory) which was identified by mass spectroscopy and $^1H$—NMR spectroscopy as trimeric 1-pyrroline.

The trimeric 1-pyrroline was characterized in the form of 4-amino-butyraldehyde p-nitrophenylhydrazone hydrochloride melting at 213° C. (according to literature 217° C.) as described by A. Lüttringhaus et al., Chem.Ber. 92, 1956 (1956).

EXAMPLE 13

25.8 g (0.2 mol) of 1-formyl-2-methoxy-pyrrolidine and 150 ml of 2N hydrochloric acid were stirred for 4 hours at 60° C., the water was removed under reduced pressure, the product taken up in methanolic HCl (about 0.01 mol HCl) and the reaction mixture obtained was added dropwise to a solution of 20 g of KOH (85%, 0.3 mol) in absolute methanol. The solvent was removed, the residue taken up in 25% aqueous sodium hydroxide solution and extracted with dichloromethane, whereupon a product was obtained from which 6.5 g (47.1% of the theory) of trimeric 1-pyrroline boiling at 150° C./15 mbar could be obtained by distillation in vacuum.

EXAMPLE 14

28.6 g (0.2 mol) of 1-formyl-2-methoxy-piperidine and 12 g of sodium hydroxide (0.3 mol) were stirred for 6 hours at 80° C. in 100 ml of water. The reaction mixture was then extracted with dichloromethane and 16.4 g (99% of the theory) of α-tripiperidein were obtained in the form of an oily extract which solidified during the course of a few hours and melted at 53° C.

EXAMPLE 15

28.6 g (0.2 mol) of 1-formyl-2-methoxypiperidine and 12 g of sodium hydroxide (0.3 mol) were dissolved in 100 ml of absolute methanol and the solution was refluxed for 6 hours. Subsequently, the methanol was removed, the residue was taken up in 100 ml of water and the whole was extracted with ether. 14.6 g (88% of the theory) of α-tripiperidein were obtained in the form of an oily extract which crystallized on rubbing and melted at 59° C.

What is claimed is:

1. Process for the manufacture of aliphatic cyclic nitrogen bases of the general formula

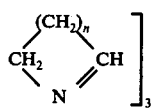 I in which n means 2 or 3, which comprises saponifying 1-acyl-2-alkoxypiperidines or pyrrolidines of the general formula

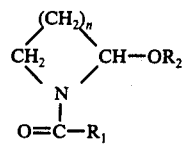 II in which n means 2 or 3

R₁ represents hydrogen or a linear or branched C₁-C₄ alkyl radical and

R₂ represents a linear or branched C₁-C₄ alkyl radical in aqueous and/or alcoholic solution in known manner in the presence of a strong acid or base and trimerizing the reaction product at a pH equal to or greater than 8.

2. A process as claimed in claim 1, wherein prior to saponification and trimerization the alcohol of formula R₂OH is split off thermally or catalytically from the 1-acyl-2-alkoxypiperidines.

3. A process as claimed in claim 1, wherein the saponification in aqueous-alcoholic or alcoholic solution is carried out in the presence of a C₁-C₄ alcohol.

4. The process of claim 3, wherein methanol is used.

5. A process as claimed in claim 1, wherein the trimerization is carried out at a pH equal to or greater than 11.

6. A process as claimed in claim 1, wherein the saponification is carried out with about 1.3 to 1.8 mols of alkali, calculated on the compound of formula II.

* * * * *